United States Patent
Pearce

(10) Patent No.: US 8,857,281 B2
(45) Date of Patent: Oct. 14, 2014

(54) DIFFERENTIAL GAS COMPONENT PROBE HAVING A PASSAGE CONTAINING A REACTION CATALYST

(75) Inventor: Robert Edmund Pearce, Lincoln Wickenby (GB)

(73) Assignee: Siemens Aktiengesellschaft, Munich (DE)

( * ) Notice: Subject to any disclaimer, the term of this patent is extended or adjusted under 35 U.S.C. 154(b) by 826 days.

(21) Appl. No.: 11/792,132

(22) PCT Filed: Nov. 29, 2005

(86) PCT No.: PCT/EP2005/056292
§ 371 (c)(1),
(2), (4) Date: Jun. 1, 2007

(87) PCT Pub. No.: WO2006/058877
PCT Pub. Date: Jun. 8, 2006

(65) Prior Publication Data
US 2008/0170964 A1    Jul. 17, 2008

(30) Foreign Application Priority Data
Dec. 4, 2004    (GB) .................................... 0426656.5

(51) Int. Cl.
*G01N 1/22*    (2006.01)
*G01N 1/26*    (2006.01)
(52) U.S. Cl.
CPC ................................... *G01N 1/2247* (2013.01)
USPC ........ 73/863.31; 73/23.2; 73/863; 73/864.81; 422/83; 422/93; 422/98

(58) Field of Classification Search
USPC ............... 73/23.2, 863.31; 422/80, 83, 93, 98
See application file for complete search history.

(56) References Cited

U.S. PATENT DOCUMENTS

| | | | | |
|---|---|---|---|---|
| 3,254,966 A | * | 6/1966 | Bloch et al. ................... | 422/171 |
| 3,768,982 A | * | 10/1973 | Kitzner et al. ................ | 422/174 |
| 3,967,933 A | * | 7/1976 | Etess et al. .................... | 436/118 |
| 3,997,297 A |  | 12/1976 | Jenkins et al. |  |
| 4,315,753 A |  | 2/1982 | Bruckenstein et al. |  |
| 4,432,939 A |  | 2/1984 | Watanabe et al. |  |
| 4,822,564 A |  | 4/1989 | Howard |  |
| 5,458,010 A | * | 10/1995 | Traina et al. ............... | 73/864.12 |
| 5,633,170 A | * | 5/1997 | Neti .............................. | 436/116 |

(Continued)

FOREIGN PATENT DOCUMENTS

| | | |
|---|---|---|
| DE | 101 21 262 A1 | 11/2002 |
| DE | 10121262 A1 | 11/2002 |

(Continued)

*Primary Examiner* — In Suk Bullock
*Assistant Examiner* — Robert Eom

(57) ABSTRACT

A probe for use in determining the amount of a first gas component in a combustion gas containing the first gas component and a second gas component which is obtainable from the first gas component by reduction or oxidation, the probe comprising: a first component probe for taking a first sample of the gas and converting the first gas component present in the first sample to the second gas component, the first component probe including a first passage for conveying the first sample, the wall of the first passage in contact with the first sample being made of a material that converts the first gas component to the second gas component; and a second component probe for taking a second sample of the gas, the second component probe including a second passage for conveying the second sample.

15 Claims, 1 Drawing Sheet

(56) References Cited

U.S. PATENT DOCUMENTS

| | | | |
|---|---|---|---|
| 5,703,299 A * | 12/1997 | Carleton et al. | 73/863.83 |
| 6,346,419 B1 | 2/2002 | Ryerson et al. | |
| 6,701,707 B1 | 3/2004 | Upadhyay et al. | |
| 2001/0019844 A1 | 9/2001 | Kishkovich et al. | |
| 2004/0040289 A1 | 3/2004 | Mazur et al. | |
| 2004/0133116 A1 | 7/2004 | Abraham-Fuchs et al. | |
| 2004/0226281 A1 | 11/2004 | Coillard | |
| 2006/0039826 A1 * | 2/2006 | Nakatani et al. | 422/68.1 |

FOREIGN PATENT DOCUMENTS

| | | |
|---|---|---|
| JP | 61064181 A | 4/1986 |
| JP | 01161149 A | 6/1989 |
| JP | 03080838 A | 4/1991 |
| JP | 05043931 A | 2/1993 |
| JP | 06115903 A | 4/1994 |
| JP | 11311613 A | 11/1999 |
| JP | 2000155115 A | 6/2000 |

* cited by examiner

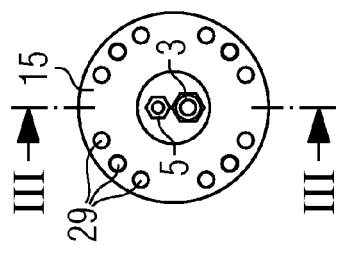
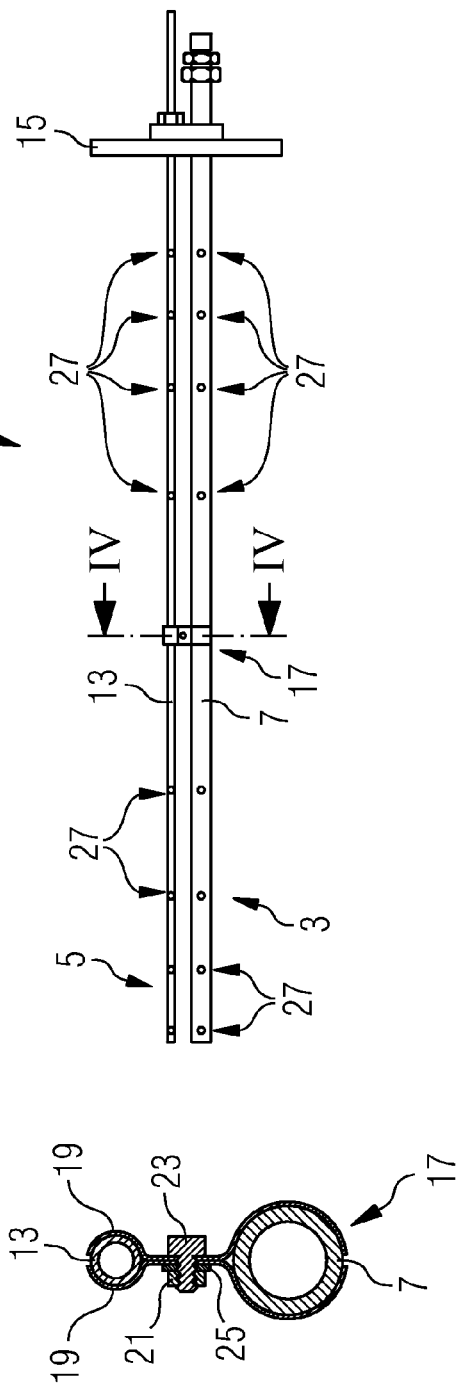
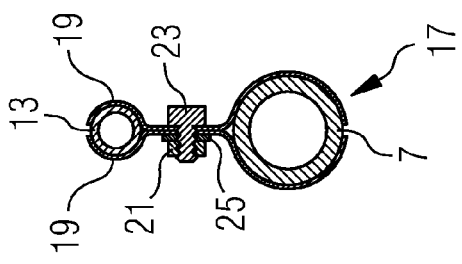
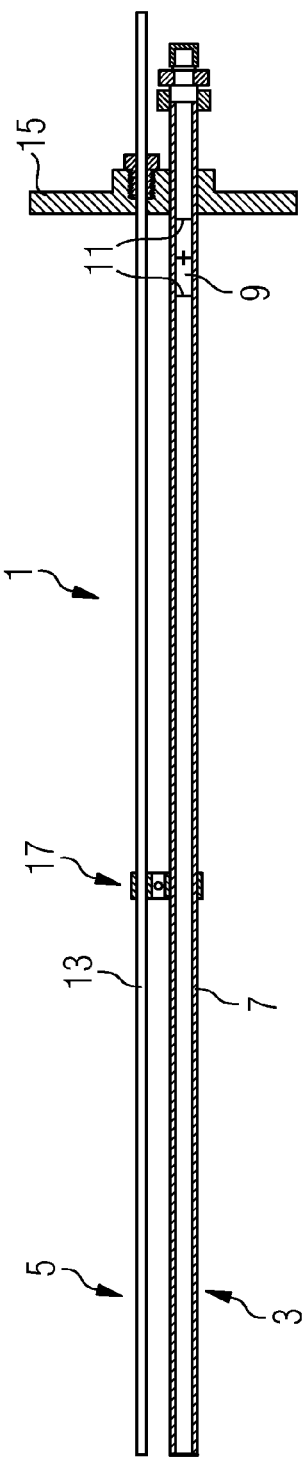

DIFFERENTIAL GAS COMPONENT PROBE HAVING A PASSAGE CONTAINING A REACTION CATALYST

CROSS REFERENCE TO RELATED APPLICATIONS

This application is the US National Stage of International Application No. PCT/EP2005/056292, filed Nov. 29, 2005 and claims the benefit thereof. The International Application claims the benefits of British application No. 0426656.5 filed Dec. 4, 2004, both of the applications are incorporated by reference herein in their entirety.

FIELD OF INVENTION

This invention relates to a probe for use in determining the amount of a first gas component in a gas.

More particularly, the invention relates to a probe for use in determining the amount of a first gas component in a gas containing the first gas component and a second gas component which is obtainable from the first gas component by reduction or oxidation.

The invention finds particular application in the determination of the amount of NO2 in a gas containing NO2 and NO.

BACKGROUND OF THE INVENTION lit is required to measure the NOX (nitrogen oxides) emissions produced by combustion plant to ensure that environmental standards are met. The two most important constituents of NOX are NO (nitric oxide) and NO2 (nitrogen dioxide). NO is usually the predominant specie but NO2 is far more toxic and reactive. Currently to measure accurately NOX at low levels extractive gas analysis must be used. A probe extracts a sample of the emissions, and a transfer line conveys the sample to measurement instrumentation which measures the NO and NO2 content. It has been found that the materials of which the probe and transfer line are made may alter the emission sample so that the measurement instrumentation does not give an accurate measure of NO/NO2 content. A metallic probe may convert NO2 to NO resulting in an artificially low measure of NO2. This especially occurs at high temperatures, i.e. temperatures of 500 degrees Celsius and above as found for example in a gas turbine engine exhaust. The material of the transfer line may absorb NO2, for example a transfer line made of polytetrafluoroethylene (PTFE). In contrast to NO2, NO is very stable. In conclusion, current approaches to measuring NOX tend to under-measure total NOX and especially NO2.

SUMMARY OF INVENTION

According to a first aspect of the present invention there is provided a probe for use in determining the amount of a first gas component in a gas containing the first gas component and a second gas component which is obtainable from the first gas component by reduction or oxidation, the probe comprising: a first component probe for taking a first sample of the gas and converting the first gas component present in the first sample to the second gas component; and a second component probe for taking a second sample of the gas, the difference between the total amount of the second gas component present in the first sample following the conversion and the total amount of the second gas component present in the second sample constituting a measure of the amount of the first gas component present in the gas.

The first gas component may be NO2 and the second gas component NO.

Preferably: the first component probe includes a first passage for conveying the first sample, and the wall of the first passage in contact with the first sample is made of a material that converts NO2 to NO; and the second component probe includes a second passage for conveying the second sample, and the wall of the second passage in contact with the second sample is made of a material that is inert as regards the conversion of NO2 to NO.

The first component probe may further comprise a converter for converting NO2 to NO, the converter being made of the same material as the wall of the first passage and being positioned in the first passage so that the first sample passes through the converter as it is conveyed along the first passage.

The wall of the first passage is suitably made of a nickel alloy that is particularly efficient at converting NO2 to NO, and the wall of the second passage is suitably made of a ceramic material such as glass.

Preferably, the first component probe comprises a first tube made of the nickel alloy, the second component probe comprises a second tube made of the ceramic material, the first and second tubes are disposed parallel and adjacent, and the first and second tubes are secured to one another such that the first tube supports the second tube.

Preferably: the first tube includes a first plurality of holes at spaced positions along its length, the first component probe taking the first sample by way of the first plurality holes; and the second tube includes a second plurality of holes at spaced positions along its length, the second component probe taking the second sample by way of the second plurality of holes.

The first and second pluralities of holes are suitably formed in the same sides of the first and second tubes and at corresponding positions along the lengths of the tubes.

According to a second aspect of the present invention there is provided a method of measuring the amount of a first gas component in a gas containing the first gas component and a second gas component obtainable from the first gas component by reduction or oxidation, the method comprising: taking a first sample of the gas, converting the first gas component present in the first sample to the second gas component, and measuring the total amount of the second gas component present in the first sample following the conversion; taking a second sample of the gas, and measuring the total amount of the second gas component present in the second sample; and subtracting the total amount of the second gas component present in the second sample from the total amount of the second gas component present in the first sample to determine the amount of first gas component present in the gas.

The first gas component may be NO2 and the second gas component NO.

BRIEF DESCRIPTION OF THE DRAWINGS

The invention will now be described, by way of example, with reference to the accompanying drawings, in which:

FIG. 1 illustrates a probe in accordance with the present invention;

FIG. 2 is an end view of the probe of FIG. 1, viewing the probe from the right in FIG. 1;

FIG. 3 is a cross-section on the line III-III in FIG. 2; and

FIG. 4 is a cross-section on the line IV-IV in FIG. 1.

DETAILED DESCRIPTION OF INVENTION

Referring to the drawings, the probe 1 comprises a first component probe 3 and a second component probe 5. Component probe 3 comprises a tube 7 made of a nickel alloy that is particularly efficient at converting NO2 to NO. Component probe 3 further comprises an NO2 to NO converter 9 comprising shavings of the same nickel alloy as tube 7 held between perforated plates 11, again of the said nickel alloy. Component probe 5 comprises a ceramic tube 13, e.g. a glass tube.

Tubes 7, 13 are disposed parallel and adjacent. Towards one end the tubes are held by a mounting plate 15. Approximately three fifths of the way along the tubes from this one end the tubes are secured to one another by means of a clamp 17. Clamp 17 comprises two halves 19 secured together by means of a nut 21, bolt 23 and washer 25. By securing tubes 7, 13 together as aforesaid the stronger nickel alloy component probe 3 supports the weaker ceramic component probe 5. Formed in the same side of tubes 7, 13 and at corresponding positions along the length of the tubes are holes 27.

Probe 1 is intended to be mounted so as to extend across the exhaust gas flow of a gas turbine engine so that holes 27 face into the gas flow. For this purpose mounting plate 15 includes fixings 29. By so mounting the probe efficient sampling takes place across the breadth of the exhaust gas flow. Sampling across the breadth of the flow accurately characterises the flow.

In use of probe 1 a heated switching arrangement, e.g. a heated solenoid valve made of inert materials, is connected to the probe to periodically switch between component probes 3, 5. A heated sample transfer line including a heated sample pump is connected to the common outlet from the heated switching arrangement to transfer samples to measurement instrumentation suitable for measuring NO. Sample integrity is maintained within the measurement instrumentation by the use of heated components.

When component probe 3 is connected to the measurement instrumentation the sample pump sucks in exhaust gas from the gas turbine engine exhaust by way of holes 27 in nickel alloy tube 7. The gas travels along tube 7 and through converter 9. The nickel alloy of the tube 7 and converter 9 operates to convert all the NO2 present in the exhaust gas to NO. It is to be noted that this conversion is assisted by the temperature of the exhaust gas. The original NO present in the exhaust gas, NO-original, together with the NO that was obtained by converting the NO2, NO-converted, is then measured by the measurement instrumentation. This provides a measurement reading NO-total equals NO-original plus NO-converted.

When component probe 5 is connected to the measurement instrumentation exhaust gas is sucked in via holes 27 in ceramic tube 13. Since ceramic is inert as regards the conversion of NO2 to NO, no NO2 will be converted to NO in component probe 5. Thus, in the case of component probe 5, the measurement instrumentation will measure only the original NO present in the exhaust gas, NO-original.

The difference between the measurements readings of component probes 3, 5 is a measure of the amount of NO2 present in the exhaust gas as there is a direct relationship between the amount of NO2 present and NO-converted. The component probe 5 measurement, NO-original, is subtracted from the component probe 3 measurement, NO-original plus NO-converted, to provide NO-converted.

In the prior art the conversion by the probe of NO2 to NO is a problem as it results in an artificially low measure of NO2. In the above described probe in accordance with the present invention, in component probe 3, this property is turned to advantage, and utilised to convert all NO2 present to NO. In the prior art the absorption of NO2 by the material of the transfer line is a problem. In the above described probe in accordance with the present invention, in the case of component probe 3, all the NO2 is converted to NO and hence there is no NO2 to be absorbed by the transfer line, and, in the case of component probe 5, any absorption of NO2 by the transfer line is of no consequence as the purpose of probe 5 is measurement of the original NO only.

The above described probe in accordance with the present invention is for use in the exhaust of a gas turbine engine, and utilises the high temperatures present in such an exhaust to assist in the conversion in component probe 3 of all the NO2 to NO. In the case where the probe is used to measure the amount of NO2 in a gas not at such high temperatures, then an additional heater would be desirable to ensure conversion of all the NO2 to NO in component probe 3.

It is to be appreciated that in the limiting case the probe described above in accordance with the present invention may be utilised to measure the amount of NO2 in a gas not containing NO, i.e. where no NO is present in the gas only NO2. In this case the component probe 5 measurement, NO-original, would be zero, and the component probe 3 measurement, NO-original plus NO-converted, would equal NO-converted, i.e. the measure of the NO2 present in the gas.

The present invention has been described above in the context of determining the amount of NO2 in a gas containing NO2 and NO. It is to be realised that the invention may also be used to determine the amount of a gas component other than NO2 (the gas component measured) where the gas contains the gas component measured and a further gas component which is obtainable from the gas component measured by reduction. For example, the invention might be used to determine the amount of SO3 (sulphur trioxide) in a gas containing SO3 and SO2 (sulphur dioxide).

The present invention has been described above in the context of determining the amount of a first gas component in a gas containing the first gas component and a second gas component obtainable from the first gas component by reduction. It is to be realised that the invention may be also be used to determine the amount of a first gas component in a gas containing the first gas component and a second gas component obtainable from the first gas component by oxidation, the reverse of reduction. Of course in this case the catalyst would be chosen for the purpose of converting the second gas component to the first gas component by oxidation. An example of this use of the invention is determination of the amount of CO (carbon monoxide) in a gas containing CO and CO2 (carbon dioxide).

The invention claimed is:

1. A probe for determining the amount of a first gas component in a flow of combustion gas containing the first gas component and a second gas component which is obtainable from the first gas component by reduction, comprising:

a first component probe configured to protrude into the flow of combustion gas for taking a first sample of the combustion gas from the flow of combustion gas and converting the first gas component present in the first sample to the second gas component, the first component probe including: a first sample inlet configured for receiving the first sample of the combustion gas from within the flow of combustion gas; and including a first passage providing fluid communication for the first sample between the first sample inlet and a location outside the flow of combustion gas, the first passage defined by an inner wall of the first component probe of the first component probe, wherein at least within the flow of combustion gas the inner wall is in contact with the first sample and is made of a material that converts the first gas component to the second gas component; and a second component probe configured to protrude into the flow of combustion gas for taking a second sample of the combustion gas from the flow of combustion gas, the second component probe including: a second sample inlet configured for receiving the second sample of the combustion gas from within the flow of the combustion gas; and including a second passage providing fluid communication for the second sample between the second sample inlet and a location outside the flow of combustion gas, the second passage defined by an inner wall of the second component probe, the inner wall of the second component probe in contact with the second sample being made of a material that is inert as to the conversion of the first gas component to the second gas component, wherein the first passage and the second passage are discrete, the difference between the total amount of the second gas component present in the first sample following the conversion and the total amount of the second gas component present in the second sample constituting a measure of the amount of the first gas component present in the gas;

wherein the first component probe further comprises a modular converter device for converting the first gas component to the second gas component positioned within the first passage so that the first sample contacts both the inner wall of the first component probe and the modular converter device as the first sample is conveyed along the first passage, wherein the modular converter device comprises shavings of a catalytic material disposed across an entire cross-section of the first passage, wherein a first end and a second end of the modular converter device each comprise a perforated plate for maintaining the modular converter device within the first passage, and wherein the inner wall of the first component probe, the perforated plates, and the shavings are made of the same catalytic material; and wherein the first gas component is $NO_2$ and the second gas component is NO.

2. A probe according to claim 1, wherein the inner wall of the first component probe is made of a nickel alloy efficient at converting $NO_2$ to NO, and the inner wall of the second component probe is made of a ceramic material.

3. A probe according to claim 2, wherein the ceramic material is glass.

4. A probe according to claim 3, wherein the first component probe comprises a first tube made of the nickel alloy, the second component probe comprises a second tube made of the ceramic material, the first and second tubes are arranged parallel and adjacent to one another, and the first and second tubes are secured to one another at a respective position along a length of the first and second tubes and at a position downstream from an end of each of the tubes such that the first tube supports the second tube.

5. A probe according to claim 4, wherein:
the first sample inlet includes a first plurality of holes at spaced positions along the length, the first component probe taking the first sample by way of the first plurality holes; and the second sample inlet includes a second plurality of holes at spaced positions along the length, the second component probe taking the second sample via the second plurality of holes.

6. A probe according to claim 5, wherein the first and second pluralities of holes are formed in the same sides of the first and second tubes and at corresponding positions along the lengths of the tubes.

7. A probe according to claim 6, wherein the probe is suitable for determining the amount of $NO_2$ present in exhaust gas produced by a gas turbine engine.

8. The probe according to claim 1, wherein the same catalytic material is a nickel alloy.

9. A probe, comprising:
a mounting plate configured to be secured proximate a flow of combustion gas:
a first component probe secured to the mounting plate, configured to protrude into the flow of combustion gas, and comprising an inner wall that defines a first passage, the first passage extending through the mounting plate, into the flow of combustion gas within the first component probe, and to a first sample inlet, the first sample inlet configured to receive a first sample of the combustion gas, wherein the inner wall of the first passage extending into the flow of combustion gas comprises a material that converts the first gas component to the second gas component; and
a second component probe secured to the mounting plate and configured to protrude into the flow of combustion gas, comprising a second passage defined by an inner wall of the second component probe, the second passage extending through the mounting plate, into the flow of combustion gas within the second component probe, and to a second sample inlet, the second sample inlet configured to receive a second sample of the combustion gas.

10. The probe of claim 9, wherein the first passage extending into the flow of combustion gas within the first component probe is in thermal communication with the combustion gas, and wherein the thermal communication expedites the conversion of the first component gas to the second component gas.

11. The probe of claim 9, wherein during operation the first component probe is configured to convert all of the first gas component to the second gas component prior to exiting the first passage.

12. The probe of claim 9, wherein the first component probe and the second component probe extend parallel to each other.

13. The probe of claim 9, wherein during operation the first component probe is secured to the second component probe within the flow of combustion gas, and wherein the first component probe provides structural support for the second component probe.

14. The probe of claim 9, further comprising a modular converter device disposed within the first passage and within the flow of combustion gas.

15. The probe of claim 9, wherein the first sample inlet and the second sample inlet are disposed at corresponding positions along respective lengths of the first component probe and the second component probe.

* * * * *